Figure 3:
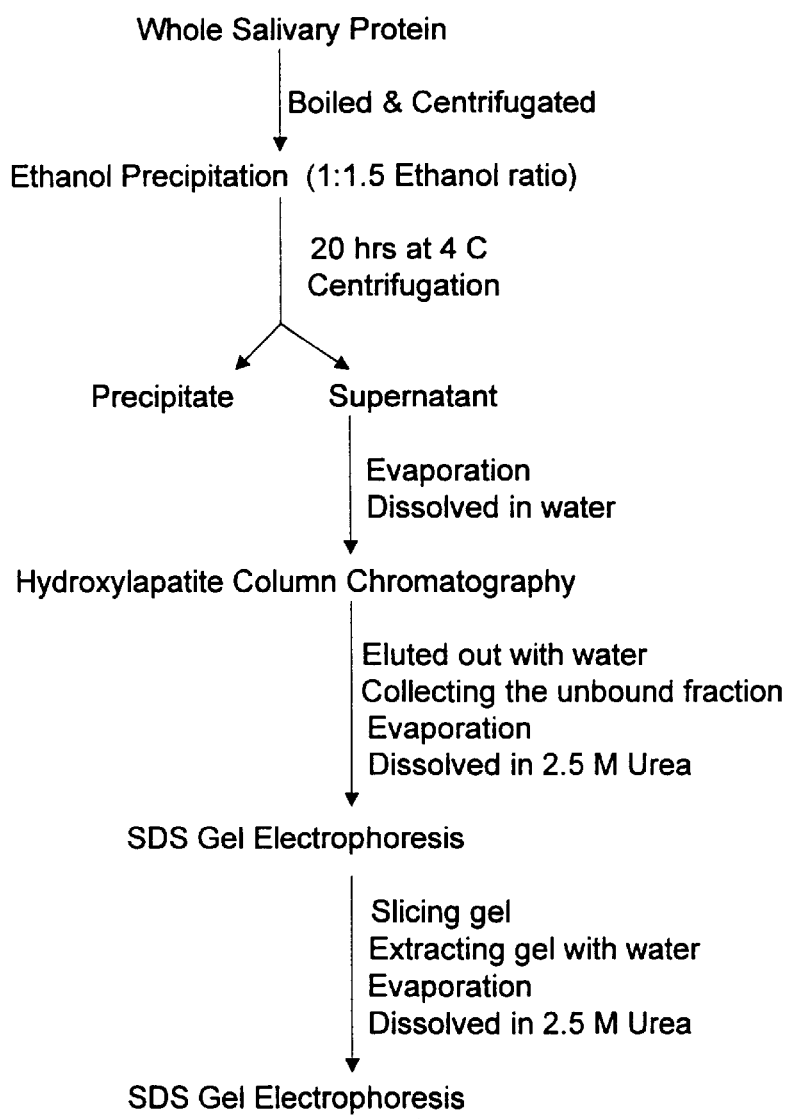

United States Patent [19]
Azen et al.

[11] Patent Number: 5,981,720
[45] Date of Patent: Nov. 9, 1999

[54] HUMAN SALIVARY PROTEINS AND FRAGMENTS THEREOF HAVING ALPHA-GLUCOSIDASE INHIBITORY ACTIVITY

[76] Inventors: Edwin A. Azen, 7080 Applewood Dr., Madison, Wis. 53719; David Pan, 19D University Houses, Madison, Wis. 53705

[21] Appl. No.: 08/925,237

[22] Filed: Sep. 8, 1997

Related U.S. Application Data

[60] Provisional application No. 60/024,712, Sep. 9, 1996.

[51] Int. Cl.$^6$ .............................. C08H 1/00; C07K 14/00
[52] U.S. Cl. ......................... 530/412; 530/350; 530/300; 514/12
[58] Field of Search ..................................... 530/350, 399, 530/300, 412; 514/2, 12, 18

[56] References Cited

U.S. PATENT DOCUMENTS

| | | | |
|---|---|---|---|
| 4,795,739 | 1/1989 | Lifson et al. | 514/8 |
| 5,089,520 | 2/1992 | Fleet et al. | 514/425 |
| 5,097,023 | 3/1992 | Ducep et al. | 536/17.4 |
| 5,157,116 | 10/1992 | Ducep et al. | 514/25 |
| 5,260,447 | 11/1993 | Nakajima et al. | 548/222 |
| 5,264,356 | 11/1993 | Rohrschneider et al. | 435/236 |

OTHER PUBLICATIONS

Fenouillet and Gluckman, Effect of glucosidase inhibitor on the bioactivity and immnunoreactivity of human immunodeficiency virus type 1 envelope glycoprotein, J. Gen. Virol. 72: 1919–26 (1991). Published sufficiently before filing date that the month is not in issue.

Santeusanio and Compagnucci, A risk–benefit appraisal of acarbose in the management of non–insulin dependent diabetes mellitus, Drug Safety 11 (6): 432–44 )1994). Published sufficiently before filing date that the month is not in issue.

Ratner, Glucosidase inhibitors for treatment of HIV–1 infection, AIDS Research and Human Retroviruses 8(2): 165–72 (1992). Published sufficiently before filing date that the month is not in issue.

Mohan, Anti–AIDSa drug development: Challenges and strategies, Pharm. Res. 9(6): 703–711 (1992). Published sufficiently before filing date that the month is not in issue.

Ratner and Heyden, Mechanism of action on N–nutyl deoxynorjirimycin in inhibiting HIV–1 infection and activity in combination with nucleoside analogs, AIDS Research and Human Retroviruses 9(4): 291–96 (1993). Published sufficiently before filing date that the month is not in issue.

Rios, Acarbose and insulin therapy in type 1 diabetes mellitus, E.J. Clin. Invest. 24, Supp. 3: 36–9 (1994). Published sufficiently before filing date that the month is not in issue.

Bischoff, Pharmacology of α–glucosidase inhibition, E. J. Clin. Invest. 24: Supp. 3: 3–10 (1994). Published sufficiently before filing date that the month is not in issue.

Kim et al., The structure and evolution of the human salivary proline–rich protein gene family, Mammalian Genome 4: 3–14 (1993). Published sufficiently before filing date that the month is not in issue.

Jacob, Aminosugar inhibitors as anti–HIV agents, in carbohydrates and carbohydrate polymers, analysis, biotechnology, modification, antiviral, biomedical, and other applications, edited by M. Yalpani, ATL Press (1993). Published sufficiently before filing date that the month is not in issue.

Toller, Nutritional recommendations for diabetic patients and treatment with α–glucosidase inhibitors, Drugs 44 Supp. 3: 13–20 (1992). Published sufficiently before filing date that the month is not in issue.

Rachman and Turner, Drugs on the horizon for treatment of type–2 diabetes, Diabetic Medicine 12: 467–78 (1995). Published sufficiently before filing date that the month is not in issue.

Azene et al. 1984 Biochem. Genetics. 22(1/2): 1–19.

*Primary Examiner*—Karen Cochrane Carlson
*Attorney, Agent, or Firm*—Michael Best & Friedrich, LLP

[57] ABSTRACT

Isolation of the salivary basic glycoproteins CON-1 and CON-2 in high purity and without substantial loss of activity was achieved in a method utilizing two denaturing steps which limit proteolysis. Cloning of CON-1 and CON-2 from the PRB2 and PRB1 genes also provides a recombinant source of the proteins, which are useful inhibitors of alpha-glucosidases in the treatment of diabetes and in preventing retroviral infection. Subfragments of CON-1 and CON-2 having alpha-glucosidase inhibitory activity are identified which can be prepared synthetically in commercial-scale quantities.

5 Claims, 13 Drawing Sheets

FIG. 1A

CON 1

```
TCT CCT CCA GGA AAG CCA CAA GGA CCA CCC CCA CAA GGA GGC AAC CAG CCC CAA GGT CCC CCA
Ser Pro Pro Gly Lys Pro Gln Gly Pro Pro Pro Gln Gly Gly Asn Gln Pro Gln Gly Pro Pro    63

CCT CCT CCA GGA AAG CCA CAA GGA CCA CCC CCA CAA GGA GGC AAC AAA CCT CAA GGT CCC CCA
Pro Pro Pro Gly Lys Pro Gln Gly Pro Pro Pro Gln Gly Gly Asn Lys Pro Gln Gly Pro Pro    126

CCT CCA GGA AAG CCA CAA GGA CCA CCC CCA CAA GGA GAC AAC AAG TCC CAA AGT GCC CGA
Pro Pro Gly Lys Pro Gln Gly Pro Pro Pro Gln Gly Asp Asn Lys Ser Gln Ser Ala Arg        186

TCT CCT CCA GGA AAG CCA CAA GGA CCA CCC CCA CAA GGC AAC CAG CCC CAA GGT CCC CCA
Ser Pro Pro Gly Lys Pro Gln Gly Pro Pro Pro Gln Gly Asn Gln Pro Gln Gly Pro Pro        249

CCT CCT CCA GGA AAG CCA CAA GGA CCA CCC CCA AAA TCT CAA GGT CCC CCA
Pro Pro Pro Gly Lys Pro Gln Gly Pro Pro Pro Lys Ser Gln Gly Pro Pro                    312

CCT CCA GGA AAG CCA CAA GGA CCA CCC CCA CAA GGA GGC AGC AAG TCC CGA AGT TCT CGA
Pro Pro Gly Lys Pro Gln Gly Pro Pro Pro Gln Gly Gly Ser Lys Ser Arg Ser Ser Arg        372
```

FIG. 1B

CON 2

```
TCT CCT CCA GGA AAG CCA CAA GGA CCA CCC CCA CAA GGA GGT AAC CAA CCC CAA GGT CCC CCA
Ser Pro Pro Gly Lys Pro Gln Gly Pro Pro Pro Gln Gly Gly Asn Gln Pro Gln Gly Pro Pro    63

CCT CCT CCA GGA AAG CCA CAA GGA CCA CCC CCA CAA GGA GGC AAC CCT CAG GGT CCC CCA
Pro Pro Pro Gly Lys Pro Gln Gly Pro Pro Pro Gln Gly Gly Asn Pro Gln Gly Pro Pro        126

CCT CCA GGA AAG CCA CAA GGA CCA CCC CCA CAA GGA GGC AAC AAA TCT CAA GGT CCC CCA CCT
Pro Pro Gly Lys Pro Gln Gly Pro Pro Pro Gln Gly Gly Asn Lys Ser Gln Gly Pro Pro Pro    189

CCA GGA AAG CCA CAA GGA CCA CCC CCA CAA GGA GGC AGC AAG TCC CGA AGT TCT CGA
Pro Gly Lys Pro Gln Gly Pro Pro Pro Gln Gly Gly Ser Lys Ser Arg Ser Ser Arg            256

Pro Gly Lys Pro Gln Gly Pro Pro Pro Gln Gly Gly Ser Lys Ser Arg Ser Ser Arg
```

FIG. 2

| | | |
|---|---|---|
| 142 | SPPGKPQGPPPQGGNQPQGPPPPPGKPQGPPPQGGNKPQGPPPPGKPQGP | 191 |
| 120 | SPPGKPQGPPPQGGNQPQGPPPPPGKPQGPPPQGGNKPQG.......... | 159 |
| 192 | PPQGDNKSQSARSPPGKPQGPPPQGGNQPQGPPPPPGKPQGPPPQGGNKS | 241 |
| 160 | ................................PPPPGKPQGPPPQGGNKS | 177 |
| 242 | QGPPPPGKPQGPPPQGGSKSRSSR  265 | |
| 178 | QGPPPPGKPQGPPPQGGSKSRSSR  201 | |

Figures 4A, 4B:
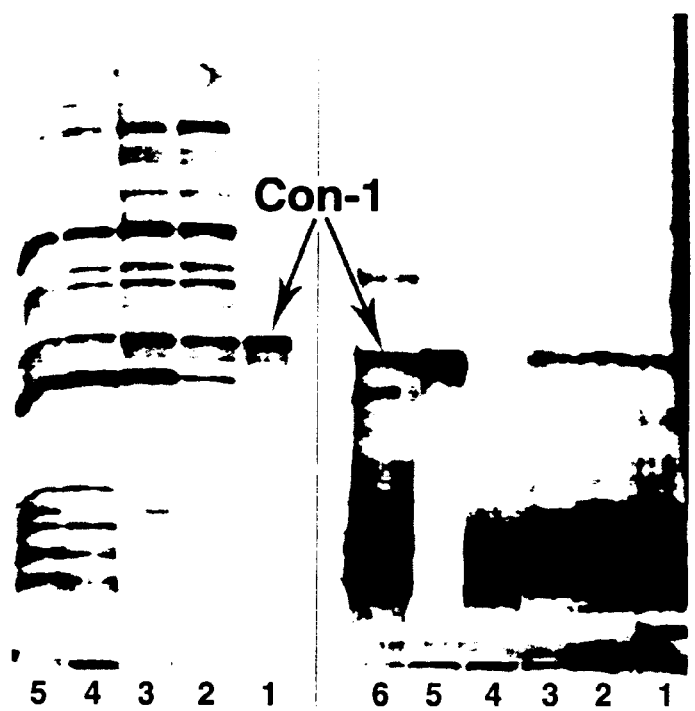

Fig. 4  Lane 1. Crude extract
2. Heat treatment saliva
3. After ethanol precipitation
4. After hydroxylapatite column
5. Slice gel extract
6. Standard parotid saliva
Arrows indicate the purified Con-1 glycoprotein 1. Standard parotid saliva protein
2. Purified Con-1 glycoprotein Inhibition of alpha-glucosidase activity by con-1

A. Con-1 protein
B. Bovine serum albumin

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..372

(xi) SEQUENCE DESCRIPTION: SEQ ID NO:1:

```
TCT CCT CCA GGA AAG CCA CAA GGA CCA CCC CCA CAA GGA GGC AAC CAG        48
Ser Pro Pro Gly Lys Pro Gln Gly Pro Pro Pro Gln Gly Gly Asn Gln
 1               5                  10                  15

CCC CAA GGT CCC CCA CCT CCT CCA GGA AAG CCA CAA GGA CCA CCC CCA        96
Pro Gln Gly Pro Pro Pro Pro Pro Gly Lys Pro Gln Gly Pro Pro Pro
                20                  25                  30

CAA GGA GGC AAC AAA CCT CAA GGT CCC CCA CCT CCA GGA AAG CCA CAA       144
Gln Gly Gly Asn Lys Pro Gln Gly Pro Pro Pro Pro Gly Lys Pro Gln
            35                  40                  45

GGA CCA CCC CCA CAA GGA GAC AAC AAG TCC CAA AGT GCC CGA TCT CCT       192
Gly Pro Pro Pro Gln Gly Asp Asn Lys Ser Gln Ser Ala Arg Ser Pro
        50                  55                  60

CCA GGA AAG CCA CAA GGA CCA CCC CCA CAA GGA GGC AAC CAG CCC CAA       240
Pro Gly Lys Pro Gln Gly Pro Pro Pro Gln Gly Gly Asn Gln Pro Gln
 65                  70                  75                  80

GGT CCC CCA CCT CCT CCA GGA AAG CCA CAA GGA CCA CCC CCA CAA GGA       288
Gly Pro Pro Pro Pro Pro Gly Lys Pro Gln Gly Pro Pro Pro Gln Gly
                85                  90                  95
```

```
GGC AAC AAA TCT CAA GGT CCC CCA CCT CCA GGA AAG CCA CAA GGA CCA         336
Gly Asn Lys Ser Gln Gly Pro Pro Pro Pro Gly Lys Pro Gln Gly Pro
            100                 105                 110

CCC CCA CAA GGA GGC AGC AAG TCC CGA AGT TCT CGA                         372
Pro Pro Gln Gly Gly Ser Lys Ser Arg Ser Ser Arg
        115                 120
```

(2) INFORMATION FOR SEQ ID NO:2:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:2:

```
Ser Pro Pro Gly Lys Pro Gln Gly Pro Pro Gln Gly Gly Asn Gln
 1               5                  10                  15

Pro Gln Gly Pro Pro Pro Pro Gly Lys Pro Gln Gly Pro Pro
            20                  25                  30

Gln Gly Gly Asn Lys Pro Gln Gly Pro Pro Pro Gly Lys Pro Gln
            35                  40                  45

Gly Pro Pro Pro Gln Gly Asp Asn Lys Ser Gln Ser Ala Arg Ser Pro
        50                  55                  60

Pro Gly Lys Pro Gln Gly Pro Pro Gln Gly Gly Asn Gln Pro Gln
 65                 70                  75                  80

Gly Pro Pro Pro Pro Gly Lys Pro Gln Gly Pro Pro Gln Gly
            85                  90                  95

Gly Asn Lys Ser Gln Gly Pro Pro Pro Gly Lys Pro Gln Gly Pro
            100                 105                 110

Pro Pro Gln Gly Gly Ser Lys Ser Arg Ser Ser Arg
        115                 120
```

(2) INFORMATION FOR SEQ ID NO:3:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..246

(xi) SEQUENCE DESCRIPTION: SEQ ID NO:3:

```
TCT CCT CCA GGA AAG CCA CAA GGA CCA CCC CCA CAA GGA GGT AAC CAA         48
Ser Pro Pro Gly Lys Pro Gln Gly Pro Pro Gln Gly Gly Asn Gln
 1               5                  10                  15

CCC CAA GGT CCC CCA CCT CCT CCA GGA AAG CCA CAA GGA CCA CCC CCA         96
Pro Gln Gly Pro Pro Pro Pro Pro Gly Lys Pro Gln Gly Pro Pro Pro
            20                  25                  30

CAA GGA GGC AAC AAA CCT CAG GGT CCC CCA CCT CCA GGA AAG CCA CAA         144
Gln Gly Gly Asn Lys Pro Gln Gly Pro Pro Pro Pro Gly Lys Pro Gln
            35                  40                  45

GGA CCA CCC CCA CAA GGA GGC AAC AAA TCT CAA GGT CCC CCA CCT CCA         192
Gly Pro Pro Pro Gln Gly Gly Asn Lys Ser Gln Gly Pro Pro Pro Pro
        50                  55                  60

GGA AAG CCA CAA GGA CCA CCC CCA CAA GGA GGC AGC AAG TCC CGA AGT         240
Gly Lys Pro Gln Gly Pro Pro Pro Gln Gly Gly Ser Lys Ser Arg Ser
 65                 70                  75                  80
```

```
TCT CGA                                                      246
Ser Arg (2) INFORMATION FOR SEQ ID NO:4:

(i) SEQUENCE CHARACTERISTICS:
        (A) LENGTH: 82 amino acids
        (B) TYPE: amino acid
        (D) TOPOLOGY: linear (ii) MOLECULE TYPE: protein (xi) SEQUENCE DESCRIPTION: SEQ ID NO:4:

Ser Pro Pro Gly Lys Pro Gln Gly Pro Pro Gln Gly Gly Asn Gln
 1               5                  10                  15

Pro Gln Gly Pro Pro Pro Pro Gly Lys Pro Gln Gly Pro Pro Pro
                20                  25                  30

Gln Gly Gly Asn Lys Pro Gln Gly Pro Pro Pro Gly Lys Pro Gln
                35                  40                  45

Gly Pro Pro Pro Gln Gly Gly Asn Lys Ser Gln Gly Pro Pro Pro
            50                  55                  60

Gly Lys Pro Gln Gly Pro Pro Pro Gln Gly Gly Ser Lys Ser Arg Ser
 65                 70                  75                  80

Ser Arg (2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:5:

Gly Gly Asn Lys
```

HUMAN SALIVARY PROTEINS AND FRAGMENTS THEREOF HAVING ALPHA-GLUCOSIDASE INHIBITORY ACTIVITY

Priority based on Provisional Application 60/024,712 filed Sept. 9, 1996.

FIELD OF THE INVENTION

This invention relates to the cloning and purification of the salivary glycoproteins CON-1 and CON-2. The invention also relates to methods utilizing CON-1 and CON-2 and fragments thereof to treat patients with diabetes or patients infected with retroviruses such as the Human Immunodeficiency Virus ("HIV").

BACKGROUND OF THE INVENTION

Proline-rich proteins (PRPs) make up about seventy percent of the salivary proteins. See Kim, et al., the structure and evolution of the human salivary proline-rich protein gene family, *Mammalian Genome*, 4: 3–14 (1993); Bennick A., Salivary proline-rich proteins. *Molecular and Cellular Biochemistry* 45: 83–99 (1982). The PRPs are divided into three groups (acidic, basic, and glycosylated) on the basis of their electrophoretic and chemical properties. Biological activities of PRPs include binding hydroxyapatite, calcium, and certain intraoral bacteria; mediation of adherence of microorganisms to the tooth surface; inhibition of hydroxyapatite formation; modification of lubricative properties of saliva; and detoxification of dietary tannins.

Six PRP genes code for many of the salivary PRPs. These PRPs show frequent polymorphisms. Azen, E. A., et al. *Am. J. of Human Genetics*, 58:143 (1996). Single PRP genes produce multiple PRPs by allelic variation, post-translational cleavage, and differential mRNA processing. Maeda, N., et al. *J. of Biol. Chem.*, 260:11123 (1985).

CON-1, a member of the PRP gene family, is a basic glycoprotein which binds concanavalin A. Approximately, 80 percent of the population has a form of CON-1, referred to as the large form, 10 percent the small form (CON-2), and 10 percent are missing CON-1 altogether. The CON-1 protein has proven extremely difficult to purify and characterize because of its rapid degradation in saliva.

It has been found that CON-1 and its analog, CON-2, are highly potent alpha-glucosidase inhibitors. Such inhibitors of synthetic origin have shown efficacy in treating certain medical conditions.

Alpha-glucosidases are enzymes which hydrolyze both alpha-1,4 and alpha-1,6 glycosidic linkages. Cleaving d-1,4- and d-1,6-linkages result in the conversion of non-absorbable carbohydrates into absorbable sugars during the digestion of foods. The proper post-translational processing of glycoproteins also requires cleavage of part of the oligosaccharides. Synthetic inhibitors of alpha-glucosidase have proven useful in the treatment of diabetes and show potential for the treatment of retroviral infections such as those caused by HIV.

Acarbose is an alpha-glucosidase inhibitor widely used to treat diabetic patients. Acarbose is the only new pharmaceutical therapy for non-insulin dependent diabetes that has become available in the last 40 years. See Santeusanio, et al. *Drug Safety*, 11(6):432–444, (1994), and Bischoff, H., *Eur. J. of Clin. Invest.*, 24, Suppl. 3. 3–10 (1994).

Acarbose acts by competitively inhibiting alpha-glucosidases in the intestinal brush border. Alpha-glucosidases convert nonabsorbable dietary starch and sucrose into absorbable monosaccharides. Inhibitors of alpha-glucosidase delay this conversion, resulting in the slower formation and absorption of monosaccharides. Therefore, these inhibitors reduce the concentration of postprandial blood glucose, effectively treating hyperglycemia. It has been difficult to find other metabolically active drugs that lack toxicity, as reviewed by Rachman, J., *Diabetic Medicine*, 12:467–478 (1995). Several synthetic alpha-glucosidase inhibitors have been developed as disclosed in U.S. Pat. Nos. 5,286,877, 5,260,447, 5,157,116, 5,097,023, 5,028,614, 5,004,838, and 4,898,986.

Alpha-glucosidase inhibitors also appear to be useful in the treatment of AIDS. See generally, Ratner, L., and N. Heyden, Mechanism of Action of N-Butyl Deoxynojirimycin in Inhibiting HIV-1 Infection and Activity in Combination with Nucleoside Analogs, AIDS Research and Human Retroviruses, Volume 9, Number 4, (1993); Ratner, L., Glucosidase Inhibitors for Treatment of HIV-1 Infection, AIDS Research and Human Retroviruses, Volume 8, Number 2 (1992); Mohan, P., Anti-Aids Drug Development: Challenges and Strategies, Pharmaceutical Research, Vol. 9, No. 6, (1992). The HIV-1 envelope proteins are heavily glycosylated. Much research has centered on the development of selective inhibitors of oligosaccharide synthesis and processing for use as antiviral drugs.

Alpha-glucosidase is required for proper post-translational processing of the env proteins of HIV. Oligosaccharides on the mature env glycoproteins do not play a direct role in infectivity, but infectivity depends on proper oligosaccharide processing. Without proper processing, the env proteins do not fold correctly, impairing infectivity. Fenouillet, E., et at. *J. of Gen. Virol.*, 72:1919–1926 (1991).

This research has resulted in the development of synthetic alpha-glucosidase inhibitors as disclosed in U.S. Pat. No. 5,286,877, 5,264,356, and 5,097,023. In vitro studies demonstrate these compounds inhibit the infectivity of HIV. U.S. Pat. No. 5,264,356 discloses a method of inhibiting the infectivity of HIV and other retroviruses in vitro by application of alpha-glucosidase inhibitors. One of these inhibitors, N-Butyl deoxynojirimycin, has entered clinical trials. U.S. Pat. Nos. 5,028,614 and 5,089,520 disclose methods of treating human patients infected with retroviruses, including HIV, with alpha-glucosidase inhibitors.

SUMMARY OF THE INVENTION

In accordance with the present invention, salivary protein CON-1, or its closely related analog, CON-2 is a potent alpha-glucosidase inhibitor, which is useful in preventing cellular penetration of retroviruses, and in retarding the release and uptake of excessive glucose harmful in diabetes. Thus, in one aspect of the invention, a method is provided for reducing infectivity of retroviruses by inhibiting alpha-glucosidase processing of the retroviral envelope protein required for proper engagement of the virion with its cellular receptor. Administration may be parenteral in such amounts and at such intervals that an increase in CD4 lymphocyte numbers is observed and a reduction in virus titers may be seen. There seems to be a growing utilization of viral titers as well as CD4 levels to assess HIV activity. Administration may also be local at genital and anal surfaces, where it may be a barrier for infection.

In another aspect of the invention, a method is provided for alleviating excess uptake of simple sugars in the adult onset diabetic condition, by administering orally either CON-1, CON-2 or a bioactive fragment thereof in a quantity sufficient to inhibit the breakdown of complex carbohydrates to absorbable simple sugars as determined empirically on patient by patient basis. This inhibition results from the potent anti-alpha-glucosidase activity of these proteins.

Thus, it is an object of this invention to provide a method of treating excess simple sugar uptake in adult onset type II diabetes by administering an alpha-glucosidase inhibitor strong enough to retard normal carbohydrate hydrolysis, but which is non-toxic and without adverse side effects. A further object is to exploit the alpha-glucosidase inhibitor properties of the CON-1, CON-2 proteins, and bioactive fragments thereof to intervene in the process by which retroviruses invade CD4+ lymphocytes, by administration of a naturally occurring protein which is non-immunogenic. This latter property is important because multiple serial doses of the protein or a truncated form may be necessary to adequately suppress viral penetration, to permit regeneration of the CD4+ population or prevent its further depletion, without causing an adverse immune response or other adverse reaction.

Purification of CON-1 and CON-2 has been extremely difficult because of their unusual vulnerability to proteolytic attack. In the purification method of the present invention, the crude protein preparation, either from a media containing recombinant CON-1 or CON-2, the cytoplasm of disrupted cells containing the recombinant protein, or expectorated whole saliva (or parotid gland exudate) is first heated substantially to boiling for a time sufficient to inactivate any proteases contained therein, and further purified by alcohol precipitation. These steps are followed by sorbing onto hydroxyapatite, washing to separate non-binding material, eluting the CON-1 or CON-2 from the hydroxyapatite, electrophoresing on a denaturing gel, and recovering the purified protein by eluting from the appropriate gel slices, to yield a stable, protease-free protein of 124 and 82 amino acids, respectively.

In the recombinant embodiments, the present invention comprises a recombinant DNA molecule having a promoter operably linked to the CON-1 or CON-2 encoding sequence. The sequences are set forth in FIGS. 1A and 1B for CON-1 and CON-2, respectively, designated SEQ ID NO. 1 and SEQ ID NO. 3. FIG. 2 aligns the sequences of CON-1 and CON-2 to indicate the internal deletion present in the CON-2 sequence. The recombinant sequence can be inserted into various expression vectors for in vivo production of protein, or protein may be produced in vitro in a cell-free coupled transcription/translation system.

In a further embodiment of the invention, CON-1/CON-2 is encapsulated, in a dry, aggregated form, in a protective enteric coating, to prevent degradation by salivary or gastric-dwelling proteases.

It was found that the inhibitory activity of CON-1 or CON-2 was contained in a subfragment of the native proteins. This activity is expressed in a glycosylated tetrapeptide of primary structure: glycine-glycine-asparagine-lysine, with glycosylation occuring at the asparagine residue in the form of acetylglucosamine. It is therefore an aspect of the present invention to administer the tetrapeptide reagent orally in free form or protected by an enteric coating, for the treatment of secondary diabetes by alleviating the excess uptake of simple sugars in the intestine. This reagent, together with any physiologically compatible diluent vehicle known in the art, may also be injected for treatment of retrovirus infection of any virus in which glucosidase activity plays a role in its life cycle.

In the case of injection applications, it may be desirable to utilize larger fragments of CON-1 or CON-2 on either side of the tetrapeptide active portion, to retard clearance from the bloodstream. While the small molecule nature of the tetrapeptide is desirable in that the tetrapeptide lacks immunogenicity upon repeated administration, however, such molecules are typically excreted from the kidney very rapidly. The larger fragments will contain several native residues (up to about 20–25 residues) upstream on the amino terminal end of the tetrapeptide, and/or downstream on the carboxy terminal end of the tetrapeptide to reduce clearance rate without loss of inhibitory activity. Alternatively, the tetratpeptide or larger fragment may further be conjugated to a nonimmunogenic carrier to form a carrier glycosylated tetrapeptide conjugate. Relatively short fragments (up to 50 residues) including the glycosylated tetrapeptide may be prepared synthetically in commercial quantities. Larger fragments up to the size of the native protein may be most economically prepared in commercial scale by recombinant technology.

In a further embodiment of the present invention, Applicants discovered that the inhibitory activity of the glycosylated tetrapeptide is enhanced by pyridoxylation of the carboxy terminal lysine compared to the unpyridoxylated peptide, so that an improved synthetic drug for treatment of diabetes and HIV-1 infection is provided by a reagent comprising the following primary structure:

glycine-glycine-asparagine-pyridoxyl-lysine acetylglucosamine.

BRIEF DESCRIPTION OF THE DRAWINGS

FIG. 1A and 1B are sequence diagrams giving the nucleotide sequence for CON-1 and CON-2 respectively, the corresponding derived amino acid sequence, and the position of the nucleotide and corresponding amino acid.

FIG. 2 is a sequence diagram showing the alignment of the amino acids of CON-1 and CON-2.

FIG. 3 is a flow chart depicting the steps in the purification of CON-1 and CON-2 salivary proteins.

FIG. 4A and 4B are photographs of gels showing a comparison of protein and carbohydrate staining of CON-1 at various stages of purification.

FIG. 5 is a photograph of a gel showing that CON-1 is a glycoprotein.

FIG. 6 is a bar graph comparing various carbohydrases in the presence of CON-1.

FIG. 7 is a graph showing the dose/response of alpha-glucosidase inhibition at various concentrations of CON-1.

FIG. 8 is a bar graph illustrating the effect of removing the carbohydrate moiety from CON-1 on glucosidase inhibition.

FIG. 9 is a bar graph showing the effect of CON-1 on the inhibition of HIV in culture, as measured by the detection of p24 protein.

FIG. 10 is a rectalinear plot of the G.50 column fractions obtained upon the digestion of CON-1.

FIG. 11 is a rectalinear plot of the HPLC purification profile.

FIG. 12 is a bar graph showing nontoxicity of CON-1.

DETAILED DESCRIPTION OF THE PREFERRED EMBODIMENT

The salivary proline-rich proteins (PRPs) constitute about two thirds of parotid salivary proteins containing the basic and glycosylated types. Six closely linked PRP genes, located on chromosome 12p13.2 code for these salivary proteins which show frequent polymorphisms. Although the sequences of the six genes in the aggregate are known (See Kim, et al., Mamm. Genome, 4: 3 (1993 and Kim, et al., Genomics, 6:260 (1990), the structure of two polymorphisms, CON-1 and CON-2 was not known until 1996 (See Azen, et al., Am.J.Hum.Genet., 58:143 (1996). The CON-1 and CON-2 proteins are so named because they bind concanavalin in vitro. The CON-1 glycoprotein is encoded in the PRB2 gene, and the CON-2 glycoprotein is encoded in the PRB1 gene, probably involving a gene conversion. There is also a protein having the con- phenotype, which appears to result from a single nucleotide change abolishing a putative single potential N-linked glycosylation site.

Recombinant clones were created by bacteriophage cloning into charon 40 libraries, and identified by hybridization with a HinfI 980 probe derived from exon 3 of PRB1 and which cross-hybridizes with exon 3 of all six PRP genes. (See Azen, et al., supra, Azen, et al., Maeda, Biochem. Genet. 23:455 (1985), Azen, et al., "Molecular Genetics of human salivary proteins and their polymorphisms," In Harris, et al., Eds., Advances in human genetics. Plennum, N.Y., at 141., Azen, et al., Am. J. Hum. Genetics, 50:842 (1992) all incorporated herein by reference. Subcloning was carried out in Bluescript. The subclones and deletion series utilized in sequencing are described in detail in Azen, et al., supra, 1996 article at 144–145.

This article further describes and illustrates the nucleotide sequence and deduced amino acids of exon 3 regions of PBR1 and PRB2. The portions corresponding to CON-1 and CON-2 are herein set forth in FIGS. 1A and 1B. FIG. 2 shows the relationship of the two sequences by aligning corresponding nucleotides. Dots represent the deleted portions. In preparing the appropriate fragments for cloning into an expression vector, restriction sites are selected or introduced close to the 5' and 3' ends of the coding sequence or a functionally active subfragment. In the event that new sites are preferred, appropriate site directed mutagenesis may create the desired base changes. Cloning the restriction fragments is carried out by standard methods known in the art. It may also be possible to synthesize the gene or active subfragments for incorporation into expression vectors.

For expression of the cloned restriction fragments, various eukaryotic hosts and vectors constructed from animal viruses may be selected. Since high levels of CON-1/CON-2 synthesis are desirable in commercial-scale production, the use of overproducing Baculovirus vectors are preferred. Another advantage of the Baculovirus system is that in the eukaryotic host, which may be any of the cell lines available conventionally for this purpose, eukaryotic protein modification, including glycosylation, processing, and transport readily occur. The structure of the CON-1 and CON-2 carbohydrate moieties is presently incomplete, but the contribution of this structure to the specificity of alpha-glucosidase inhibition is now unknown. Since the deglycosylated protein retains sufficient activity to be medically useful in the diabetes and retrovirus infection indications, it may be that any carbohydrate inserted at the putative glycosylation sites, will enhance inhibitory activity. The presence or absence of the carbohydrate moiety does not appear to affect protein stability.

In bacterial expression systems, the strategy for protein production is somewhat different. pGEX constructs can be prepared for the full-length proteins, or fragments thereof, by standard techniques known in the art. Fusion polypeptides can potentially be purified by adsorption onto glutathione-agarose beads, followed by elution in the presence of glutathione. In the event that protease digestion is a problem, use of protease inhibitors such as Leupeptin or Chymostatin may be employed at ambient or elevated temperatures. The extreme temperature stability of the CON-1/CON-2 proteins may also yield a relatively thermal stable fusion protein.

Another possible purification scheme in a bacterial expression system utilizes the maltose binding protein (MBP) vector. This vector contains the strong, inducible tac promoter and the malE translation initiation signal to give high-level expression of the cloned CON-1/CON-2 genes. The CON-1/CON-2 genes may be subcloned into one of the MBP vectors (pMAL-c2 or pMal-p2), and the coding sequence may be fused in frame to the 3' end of the malE gene. The vector of pMAL-c2 has an exact deletion of the malE signal sequence which leads to cytoplasmic expression without secretion into the media. Again, it may be necessary to carry out initial purification at elevated temperatures, denaturing to the fusion gene product, to prevent proteolysis. In any event, constructs using strong promoters and translation enhancer sequences, with or without signal sequences can be used without the fusion genes, to produce large quantities of the CON-1/CON-2 proteins, or fragments thereof.

These constructs can also be used to generate protein in vitro. While translation enhancers, such as pCITE, can be used, any promoter with strong fidelity to its polymerase will have efficacy in this embodiment of the present invention. Preferred promoter/polymerase systems are the promoter/polymerase combinations for SP6, T7, and T3 bactiophages. These may be used conveniently in continuous flow in vitro transcription/translation as disclosed by Baranov, et al., Gene, 84:463 (1989). The advantage of producing the protein in vitro, is that proteolysis can generally be controlled by commercially available protease inhibitors, even in the presence of proteases contained in the eukaryotic lysate.

In the purification of the CON-1 and CON-2 proteins, several schemes were attempted, including an affinity chromatography step on a concanavalin-bound matrix. While a small amount of protein was obtained, the procedure could not be scaled up to preparative amounts. Use of any conventional series of steps, i.e., gel filtration, affinity, or ion exchange chromatography failed to produce adequate yields. Based on gel electrophoresis in a denaturing SDS PAGE system, it was apparent that the characteristic CON-1,2 bands observable in the crude preparation were rapidly lost, presumably through proteolytic degradation. It was found that purification without degradation was possible only by selecting conditions which normally completely denature most human proteins.

The crude preparation (either cell lysate, whole saliva, or parotid exudate) is collected at subzero temperatures, preferably into a dry-ice chilled container. The preparation is then heated to a temperature between 75 and 100 degrees Centigrade, for a period sufficient to cause denaturation of proteases. At lower temperatures, the time of exposure to heat may be increased up to one hour. Best results are obtained by heating an aliquot of the crude preparation in boiling water from 2 to about 10 minutes. Precipitated protein is then removed by centrifugation followed by an alcohol precipitation. The alcohol may be isopropyl, methyl, or ethyl, ethyl being preferred because of its nontoxic or USP properties. Alcohol precipitation is generally carried out overnight at 4 to 15 degrees.

After a second centrifugation, the sample is evaporated to dryness, resuspended in water or other conventional diluent, and applied to hydroxyapatite, either in a bulk slurry, or preferably a column. After washing and elution with diluent, the first peak was collected and evaporated to dryness. In the case of absorption in a bulk slurry the separations may be carried out conveniently by filtration. The dry residue is then dissolved in an appropriate diluent, such as 0.5 to 5.0M urea, or other disaggregating solution, and electrophoresed on a SDS polyacrylamide (PAGE) gel. The band of CON-1 and CON-2 eluted from the gel are then dialyzed extensively to remove the SDS, and purity affirmed on an analytical SDS PAGE gel. Protein identity is routinely confirmed by conventional Western blot analysis, after transfer of the protein to a Immobilon PSQ membrane. Amido black and ConA stains detect protein and carbohydrate respectively.

From the foregoing description of the general purification procedures, it is apparent that CON-1 and CON-2 are very unusual proteins with respect to their extreme stability to denaturing conditions. These extreme steps were implemented after conventional approaches proved futile. In conventional purification strategies, the protein was either degraded too rapidly to remove contaminating proteases, or the protein is inherently unstable in the presence of alterative materials. Among those techniques attempted in purifying CON-1 and CON-2 are the following: Sephadex gel filtration, DEAE cation and anion exchange chromatography, preparative gradient SDS-gel electrophoresis, solvent precipitation in an initial step (methanol, propanol, isopropanol, butanol acetone, and phenol), concanavalin A affinity column chromatography, and blue dye gel affinity column chromatography. Possibly one or more of the offending proteases copurifies with the CON-1/CON-2 preparation, and thereby continues to degrade during purification itself.

The CON-1 and CON-2 proteins have 124 and 82 amino acids respectively, as derived from the nucleotide sequences given in FIGS. 1A and 1B. In addition, there are sites for potential glycosylation. One of them, which involves a single base substitution at position 730 is associated with the con- phenotype. Carbohydrate groups do, however, copurify with the CON-1 and CON-2 protein. The previous data (Azen, *Am. J. Human Genet.* 58:143 (1996) that glycosylation occurs at one N-linked site in both CON-1 and CON-2 proteins.

In the recombinant expression systems in which either the CON-1 or CON-2 proteins are secreted from the cells, or obtained from cell lysates, the same purification scheme may be used as for whole saliva or parotid exudate, in order to protect the protein from proteases present in the lysate, or secreted into the culture media. Another advantage of the present method of synthesis is that most of the steps are readily adapted to large-scale commercial purification.

CON-1 and CON-2 were found to have a potent inhibitory effect on alpha-glucosidases, which appear to be highly specific for this type of carbohydrase. This activity is highly specific in that its inhibition of alpha-glucosidase is nearly complete, but at the same concentration (0.02 units of yeast alpha-glucosidase) there is essentially no inhibitory effect on any of the following other carbohydrases: alpha-amylase, invertase, beta-amylase, glucoamylase, or debranching enzyme. It is also of interest that no other salivary PRP tested had this activity. Among those tested were Ps-1, Ps-2, GL-1, II-2. IB-1, IB-4. and others.

The alpha-glucosidase inhibitory activity of CON-1 and CON-2 has two very significant applications in medical indications. By reference herein to CON-1 and/or CON-2 activity, the protein fragments thereof or truncated forms of the native proteins retaining the bioactivity (alpha-glucosidase) are intended as equivalent. The first application is oral administration of CON-1 or CON-2 to alleviate excess uptake of simple sugars in diabetes. In this condition control of glucose uptake by an inhibitor can compensate for lower circulating levels of insulin or where there is a resistance to its action at the cellular level, and thereby prevent blood sugar levels from rising to potentially dangerous levels. Preferably the CON proteins or their bioactive proteins are administered in a capsule or other pharmaceutically acceptable form that creates a barrier between the protein and the proteases that are contained in saliva to which the CON proteins are unusually sensitive. Most preferably the therapeutic proteins will be packaged in a protective composition or coating which will not dissolve away freeing the protein, until it reaches the small intestine where glucosidase activity is concentrated, and where the level of endogenous proteases has subsided.

Applicants have discovered that the inhibitor activity is contained in a smaller fragment of the Con 1 or Con 2 protein. After digestion with an endopeptidase, screening of the peptide fragments for alpha-glucosidase inhibitory activity revealed one bioactive tetrapeptide fragment having a primary structure: glycine-glycine-asparagine-lysine. In the preferred embodiment, the asparagine is glycosylated by acetylglucosamine. Incubation of either the Con-1 or Con-2 proteins with N-acetylglucosaminidase results in a marked reduction in inhibitory activity. (See FIG. 8). Removal of the acetylglucosamine moiety from the tetrapeptide similarly results in marked reduction in inhibitory activity. These results indicate that the glycosylated form of the tetrapeptide/proteins optimizes the inhibitory effect, and also corroborates the structure of the tetrapeptide.

In the practice of the invention, particularly as to the use of reagents in the treatment of HIV-1 infection in which the compositions are injected into the circulation, it is desirable to present the active moiety in elongated or conjugated form, to reduce the rate of clearance from the body. Since the glucosidase inhibitory site is now known, fragments longer than the bioactive tetrapeptide fragment but shorter at each of the amino or carboxy termini than the native or unprocessed Con-1 or Con-2 proteins, may be utilized. As a practical matter, a synthetic fragment may have up to about 20–25 upstream and downstream amino acid residues homologous to the native sequence. Larger fragments may be generated in commercial quantities by recombinant techniques.

The additional amino- and carboxy-terminal residues (relative to the bioactive tetrapeptide) serves another purpose, in providing convenient functional groups for coupling of carrier molecules. Carriers are generally polymeric linear or branched chain molecules which retard clearance of the smaller conjugated oligopeptide containing the bioactive tetrapeptide, or which also impede the degradation or assimilation of the bioactive moiety. There are many examples of such carriers. Common carriers of low antigenicity include carbohydrates (dextran, starch and hydroxyethyl starch), polyalkylene units, polyvinylalcohols, polyvinylpyrrolidone, and polyethylene glycol. The latter class of compounds have been used extensively. For example, U.S. Pat. No. 4,179,377 teaches the coupling of biologically active peptides to PEG, with a resultant conjugate having dramatically reduced immunogenicity. The methods disclosed therein, and in Gnanov et al., "Macromolecules", Chapt. 17, 945 et seq. (Boston: 1987) may be used to conjugate the active fragments of CON-1 and CON-2 to achieve prolonged pharmacological action and reduced antigenicity.

Since the derivatized form of the tetrapeptide (pyridoxylated) has enhanced activity, a direct link with a carrier through the terminal lysine should maintain that activity. For carriers which, by their molecular nature, may involve a steric hindrance effect with respect to enzyme inhibition, a linker juxtaposed between the tetrapeptide and the carrier may be utilized. A convenient linker is the native protein sequence towards the carboxy-terminus of the Con proteins beginning with serine and ending with the next lysine in sequence. Conjugation through one or more of the amine groups may be accomplished by conventional coupling chemistries.

Protective enteric coatings may be applied to dried, aggregated CON-1/CON-2 proteins, with or without binding agents, and comprise conventional enteric polymers known in the art, such as cellulose acetate phthalate, hydroxypropylcellulose acetate phthalate, polyvinyl acetate phthalate, methacrylate-methacrylic acid copolymers, styrol maleic acid copolymers, and others), which remain insoluble in the stomach, but dissolve at higher pH of the intestine. For a general review of enteric coating methodology, applicable to the present invention, see Encyclopedia of Pharmaceutical Technology, Eds. Swarbrick, et al., vol. 5, pp. 189–200 (Marcel Dekker, N.Y., 1992) hereby incorporated by reference.

Various doses may be prescribed, and the size and frequency or timing of the dose may be determined empirically with each patient, according to individual levels of enzyme to be modulated, and the severity of insulin deficiency. Since CON-1 and CON-2 are naturally occurring proteins in the alimentary tract, tolerance of doses in the 50–500 mg/dose range at relatively frequent intervals (3 to 9 times daily) is to be expected. (It is also intended that CON-1/CON-2 therapy will supplement or reduce the requirement for insulin.) It has been shown previously that alpha-glucosidase inhibitors have clinical efficacy in modulating blood sugar levels, and in preventing glucose fluctuations. Such prior use of these inhibitors is reviewed in Rachman, et al., Diabetic Medicine, 12:467 (1995). The principal advantages of CON-1/CON-2 use is the lack of toxicity and the potency of the proteins.

A second major medical indication for CON-1/CON-2 use, is in the treatment of retroviral infections. It is well established that virion-receptor interactions mediating cellular penetration of the HIV and other retroviruses requires processing of the glycosidic moieties of the virion envelope by alpha-glucosidases. The presence of inhibitors of alpha-glucosidase thus interrupts this crucial processing step leading to a reduction in transmission of virus from infected to uninfected cells. More specifically, inhibitors of the post-translational glycan trimming enzyme alpha-glucosidase I show anti-HIV activity by altering glycocosylation of the envelope glycoprotein complex gp120/gp41 involved in viral/cell fusion. CON-1, especially, exerts this inhibitory effect resulting in profound reductions in signal markers of viral replication, such as production of p24 protein.

The principal alpha-glucosidase inhibitor strategies reported heretofore involve classes of synthetic compounds, or those derived from nonhuman sources. Examples include trichosanthin or momorcharin (U.S. Pat. No. 4,795,739), aminosugar compounds such as N-butyl-1-deoxynojirmycin ("Carbohydrates and Carbohydrate Polymers", in Analysis, Biotechnology, Modification, Antiviral, Biomedical and Other Applications, ATL Press: 1993), or polyhydroxydroxycyclopentane derivatives (U.S. Pat. No. 5,260,447). These all suffer from the disadvantage of being either actually or potentially toxic, or potentially immunogenic upon repeated dosing. The CON-1 is administered parenterally in a dose and at such intervals as will be effective in stabilizing the numbers of CD+ cells or reducing (stabilizing) viral titers. Since the protein is naturally occurring, continuous administration over substantial periods of time is made possible. Comparison of the dosage ranges recommended for therapeutic use in AZT and the above therapies, the corresponding CON-1 dose is 10 mg to 150 mg, assuming an average blood level of 3.0 ug/ml, and a half-life of 10 hours. An appropriate adjustment in dosage can be made for peptide fragments as a function of their molar concentration. This also assumes, based on comparable in vitro data (data not shown herein), a potency at least as great as cyclosporin. Further advantages of the present invention will be apparent from the examples which follow.

EXAMPLE 1

Purification of CON-1 or CON-2 from Human Salivary Proteins

Ten mls of whole human saliva, or for CON-2, 10 mls of parotidal exudate, were collected in a chilled beaker placed on top of dry-ice. The collected fluid was then boiled in a waterbath for 3 minutes. After centrifugation at 10,000 rpm for 5 minutes, the supernatant was collected and the proteins precipitated with ethanol (1:1.5 ethanol w/w) over night at 4 degrees C for 15 to 20 hours. The sample was then applied to a hydroxyapatite column (1.5×12 cm), which was extensively washed with distilled water. The proteins were eluted with distilled water. The first peak of eluent was collected, dried, and dissolved in 2.5 M urea solution for electrophoresis in SDS PAGE, as described in Azen, et al., Biochem. Genet., 22:1 (1984) hereby incorporated by reference.

After electrophoresis, the polyacrylamide gel was sectioned into 3 mm wide slices. The slice corresponding to the CON-1 glycoprotein was extracted twice with a total of 6 ml distilled water, and dialyzed extensively to remove the SDS. After drying, the sample was resuspended in 2.5 M urea, and its purity identified by SDS PAGE. The Western blot technique was used to transfer the protein from polyacrylamide gel onto Immodilon PSQ (Millipore Co.) prior to protein and carbohydrate staining. The protein and carbohydrate were stained with Amido black and ConA stain respectively in accordance with recommendations of the Vector Company. Only the CON-1 protein showing a single band on SDS PAGE was collected and used further.

FIGS. 4A and 4B show the bands visualized on SDS PAGE gels at various stages of purification. FIGS. 4A and B are the protein and carbohydrate stained gels respectively. The crude preparation shows, as expected, a number of bands corresponding to various glycoproteins contained in whole saliva. Fewer bands disappeared after heat treatment, indicating that in addition to inactivating proteases, there is also a loss of heat labile proteins, including glycoproteins. Finally in FIGS. 4A and 4B, a comparison of gel lanes containing crude prep and final product indicates that the CON-1 glycoprotein is purified to apparent homogeneity.

Table 1 summarizes the yields at each major step in the purification process. It also shows the increase in specific inhibitory activity of CON-1. Calculation of specific inhibitory activity from this table's entries, indicates that the specific inhibitory activity increases from about 3.8 in crude saliva to about 2810 giving about 740 fold purification with a recovery of protein of about 0.64 percent. In the practice of the invention in its disease treatment embodiments, the presence of some contaminants will not cause concern, because all species of protein present are of natural occurrence. However, the treatment steps may alter some of the non-CON-1/CON-2, so that the issue of contamination may be more important in parenteral administration (retrovirus indication) than in oral administration (diabetes indication). Therefore, the purity requirements may differ from one indication to another.

TABLE 1

| Procedures | Volume ml | Specific Inhibitory Activity | Total Protein mg |
|---|---|---|---|
| Crude Whole Saliva | 10 | 3.8 | 480 |
| After Ethanol 1 Precipitation | 3.1 | 261 | |
| Hydroxyapatite Column Chromatography | 0.8 | 76.5 | 53.6 |
| SDS Gel Electrophoresis Slice | 0.4 | 2810.0 | 3.1 |

Specific inhibitory activity is defined as the decrease of a 1 umole of glucose production from maltose as substrate per microgram of salivary protein presented in the reaction mixture per hour.

In general, given the volumes of material to be administered in the doses set forth supra, purification is largely a practical rather than a pharmacological consideration. Protein purified between 50 and 1000 fold will have efficacy in the dose volumes herein contemplated. The only critical purification criterion is that the CON-1 and CON-2 preparations be substantially protease free.

EXAMPLE 2

CON-1/CON-2 are Glycoproteins

Figure 5:
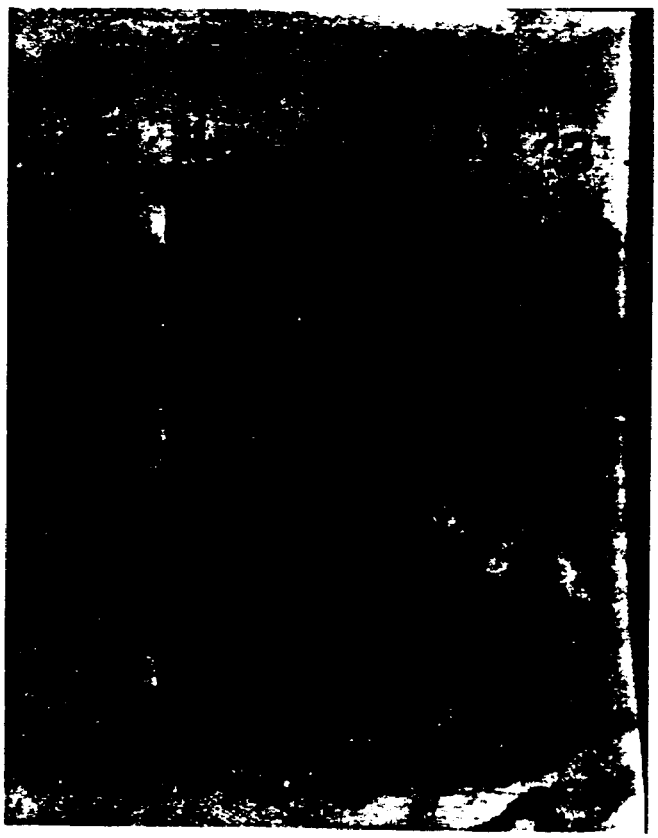

The affirmative staining of corresponding bands for protein and for carbohydrate on otherwise identically loaded and electrophoresed gels is strong evidence that the CON-1 and CON-2 proteins are, in fact, glycoproteins, as suspected from the potential N-glycosylation residues contained in the derived amino acid sequences. However, the glycoprotein character of CON-1 and CON-2 was independently confirmed. 0.01 units of carbohydrate cleavage enzyme (PNGase, source) was added to a 50 ml aliquot of purified CON-1 protein in assay buffer as recommended by the Glyko manufacturer. After a *incubation at 37° C. for 5 hours, the treated protein was loaded onto an SDS PAGE gel and compared to the native, untreated CON-1 protein. FIG. 5 is a photocopy of the gel stained with carbohydrate specific reagent. The lane 2 labelled CON-1 Glycoprotein shows a distinctive band, whereas the lane 3 on which the PNGase treated CON-1 was loaded shows an absence of a band in the native CON-1 position.

EXAMPLE 3

Activity of Various Carbohydrases in the Presence of CON-1

The following enzymes were assayed in the presence of CON-1 according to the following corresponding protocols:
Enzyme Assay of Alpha-Glucosidase Activity
The enzyme of alpha-glucosidase activity is according to the procedure as described by Sigma Chemical Company, St. Louis, Mo. Routinely, the enzyme reaction mixture contains 10 mM maltose and 50 ul of purified alpha-glucosidase or 0.02 units of yeast alpha-glucosidase in a final volume of 60 ul of 25 mM sodium acetate buffer, pH 5.6. The reaction mixture is incubated at 37° C. for 60 minutes, and the production of glucose is determined by the glucose oxidase reagent (Worthington Statzyme Glucose 500) in accordance with recommendation of Worthington Biochemical Corporation.
Enzyme Assays of Alpha- and Beta-Amylases Activity
The enzyme reactions of alpha- and beta-amylases contained 2 mg of phytoglycogen as substrate in 0.05 M sodium acetate buffer, pH 5.4; and were incubated at 37° C. for 60 minutes. The liberation of reducing sugar from phytoglycogen was measured by the reduction of 3,5-nitrosalicyclic acid as described by Bernfeld, Methods Enzymol. 1:149–158 (1955).
Enzyme Assay of Invertase
The enzyme reaction was incubated with 5 mM sucrose as substrate in 50 mM acetate buffer pH 5.0 at 37° C. for 60 minutes. The production of glucose was determined as described in "Enzyme Assay of Alpha-Glucosidase Activity".
Enzyme Assay of Debranching Enzyme
Debranching enzyme activity was determined according to the method of Lee, et al. Arch. Biochem. Biophys., 143:315–374 (1971). The reaction mixture contains 2 mg of pullulan, 100 mM sodium citrate buffer (pH 7.0), and incubated at 37° C. for 60 minutes. The reducing sugar produced from phytoglycogen was determined according to the method of Bernfeld, Methods Enzymol. 1:149–158 (1955).

Figure 6:
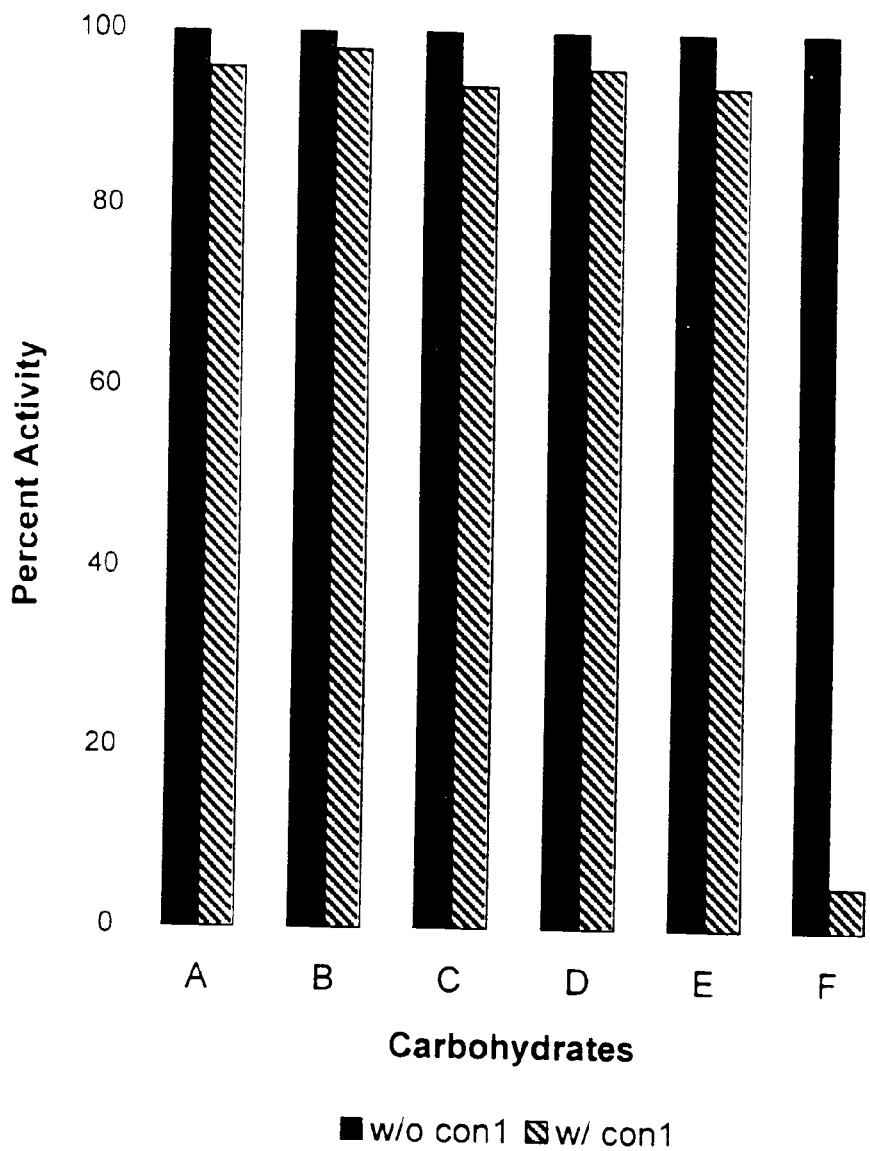

Referring to FIG. 6, it is apparent that only alpha-glucosidase shows an inhibition of essentially all enzyme activity. None of the other enzymes is significantly affected. It is concluded that the anti-carbohydrase activity of CON-1 is highly specific for alpha-glucosidase.

EXAMPLE 4

Inhibitory Effect of Various Salivary Proteins on Alpha-Glucosidase

Figure 7:
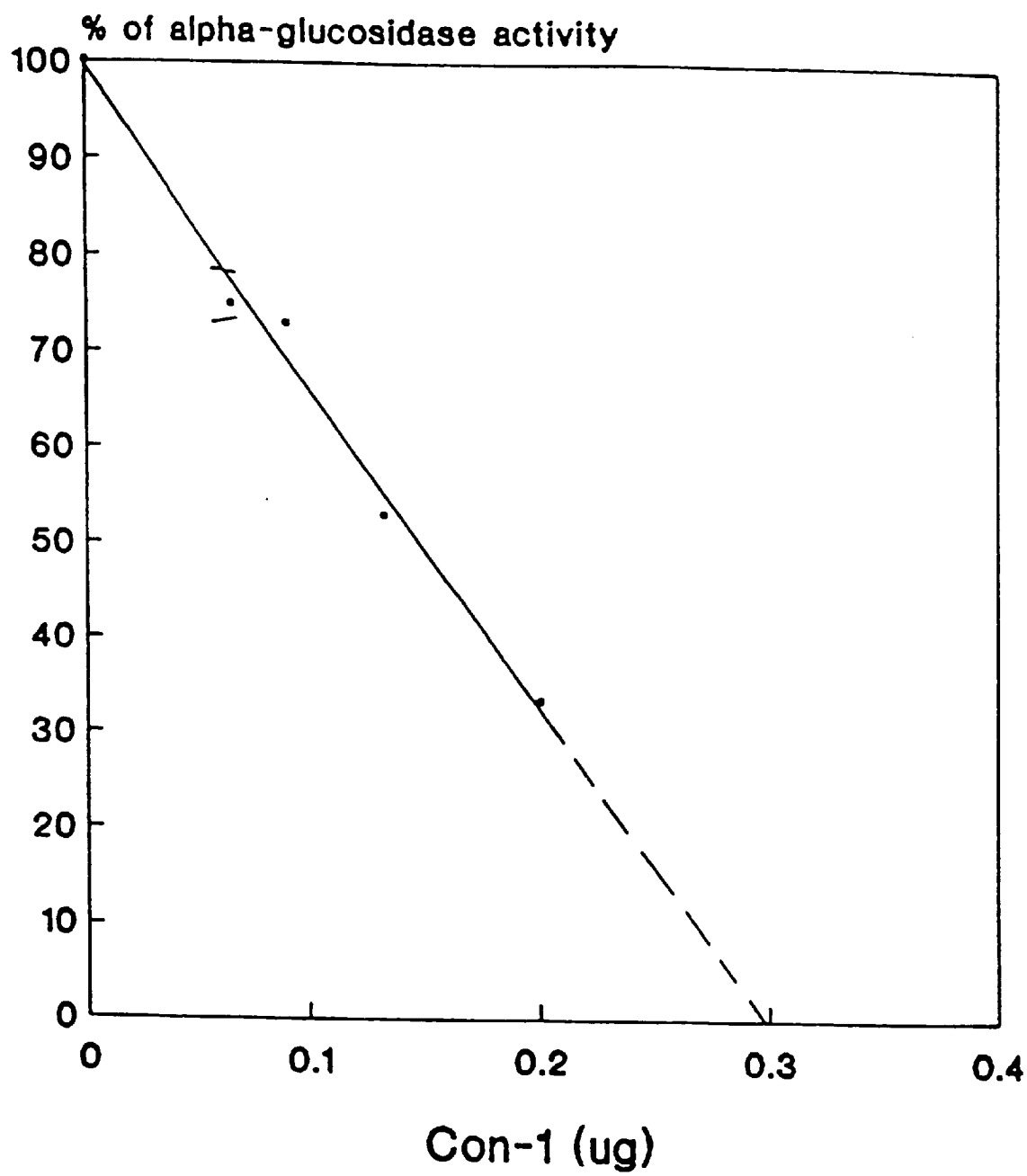

In the following experiments, alpha-glucosidase activity was measured according to the protocol set forth in Example 3. Each reaction tube contained *ug of the purified PRP obtained from saliva or parotid exudate. Table 2 shows the percentage inhibition for each such protein. Although Ps-1, Ps-2, and IB-8 showed a low level inhibition of about 20 percent, only CON-1 completely inhibited the enzyme. Three enzymes actually appeared to significantly enhance enzyme activity (alpha-amylase, IB-6, and IB-8). It is concluded that CON-1 alone among several PRP is a potent inhibitor of alpha-glucosidase. For the inhibition of alpha-glucosidase, various concentrations of CON-1 were compared for inhibitory activity against a standard amount of enzyme. FIG. 7 shows the generally linear relationship in the dose/response curve when plotting percent control activity against amount of CON-1 protein. The results suggest that about 2 to 3 molecules of CON-1 is required to completely inactivate alpha-glucosidase activity on a molar basis.

EXAMPLE 5

Effect of Removing Carbohydrate Moiety from CON-1

Figure 8:
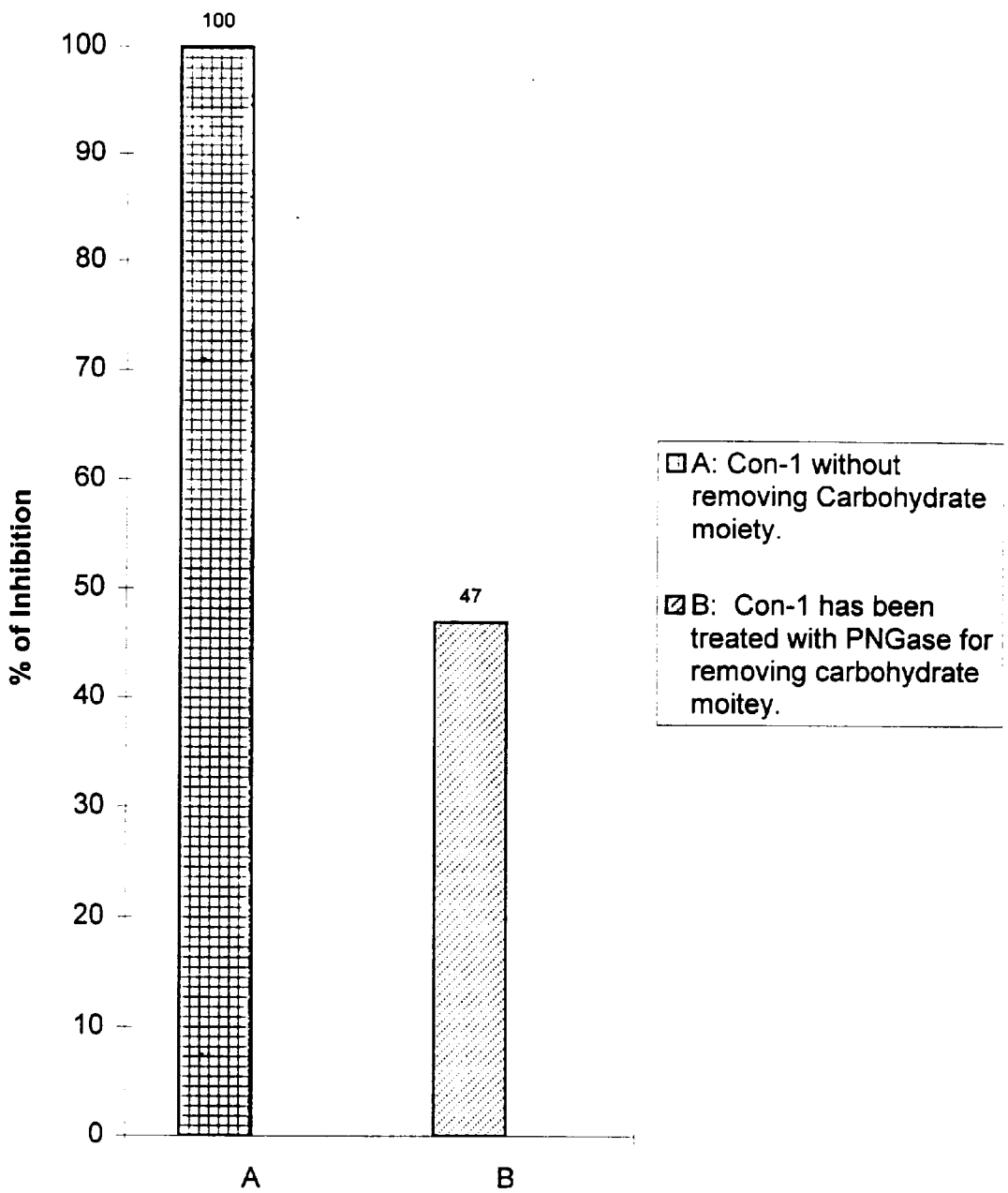
Figure 9:
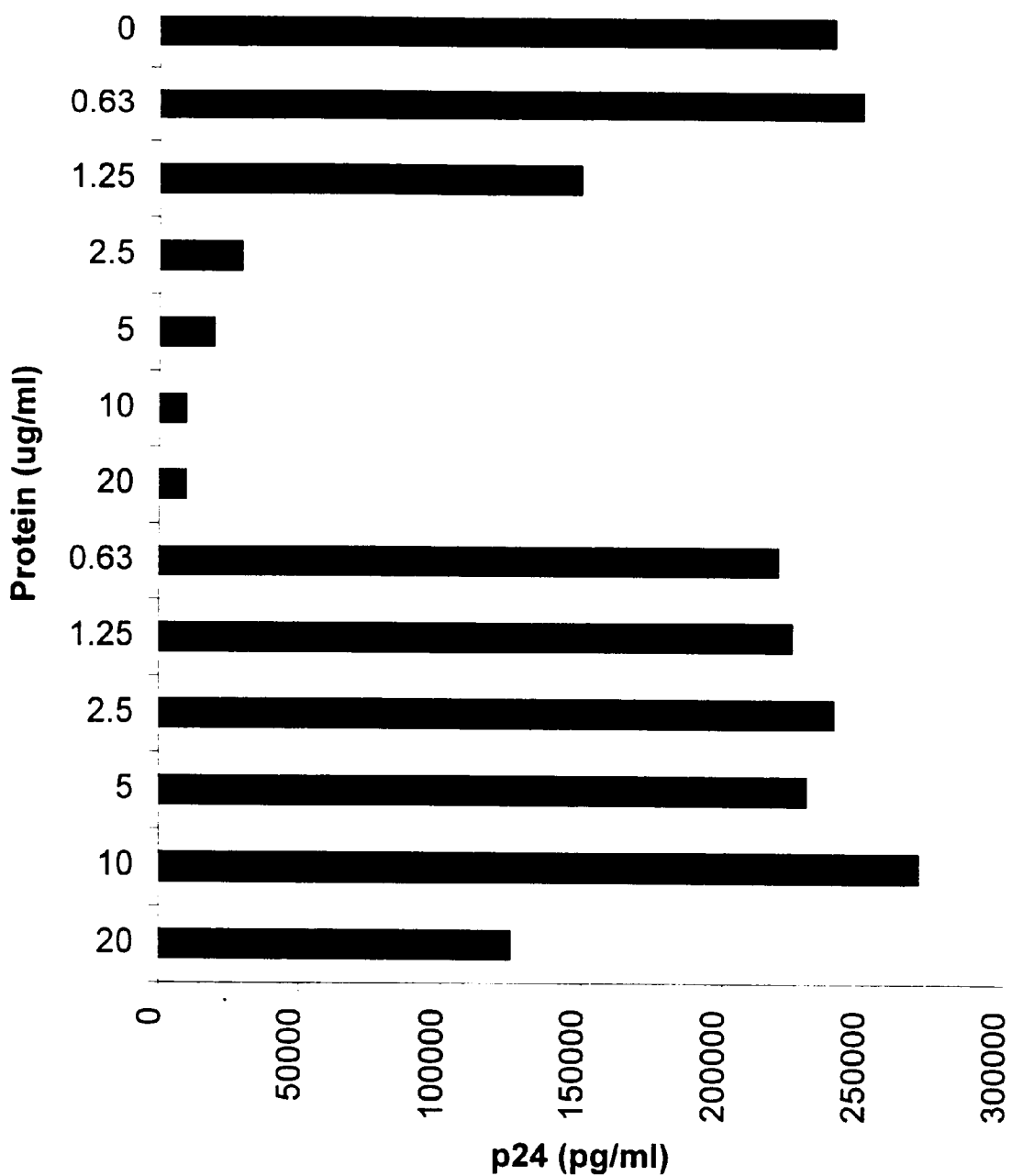
Figure 10:
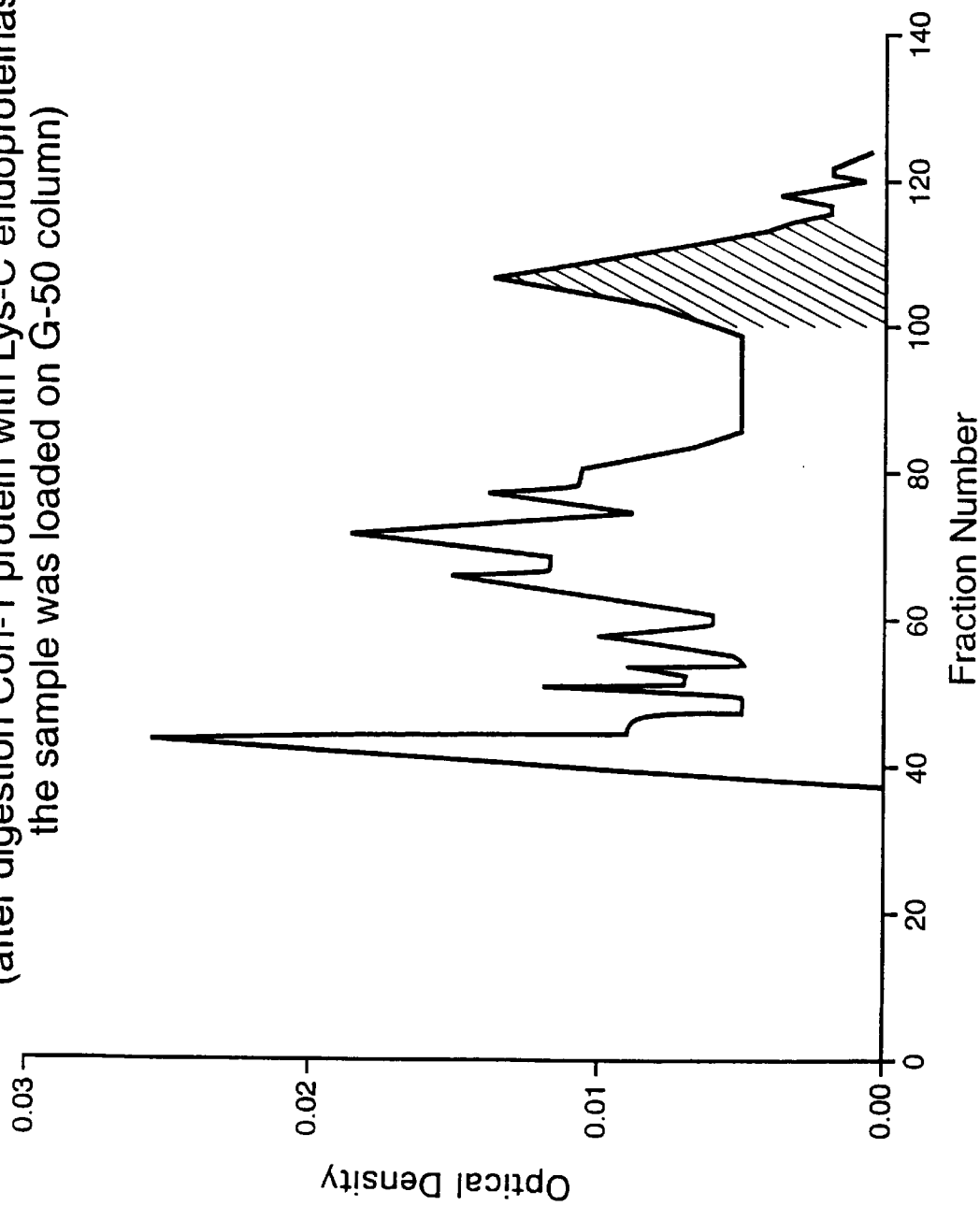
Figure 11:
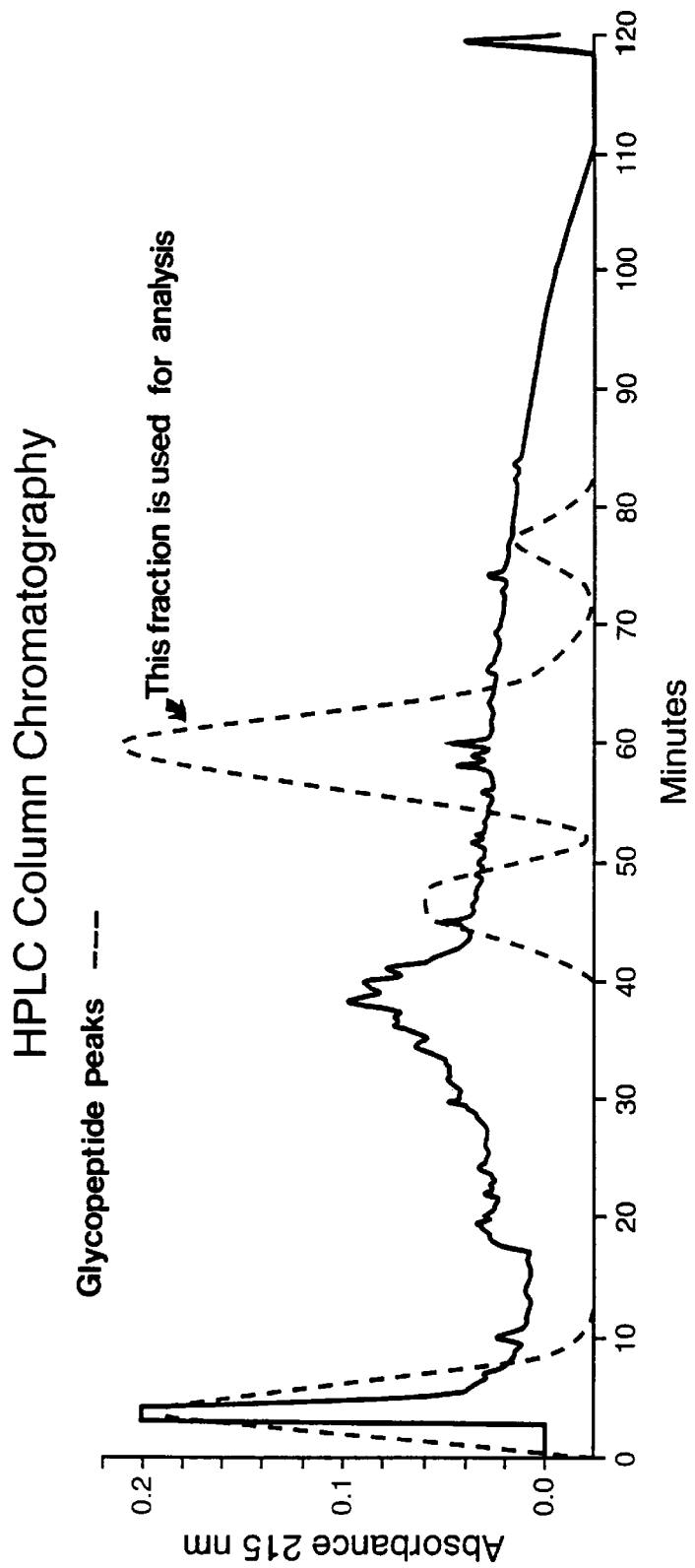
Figure 12:
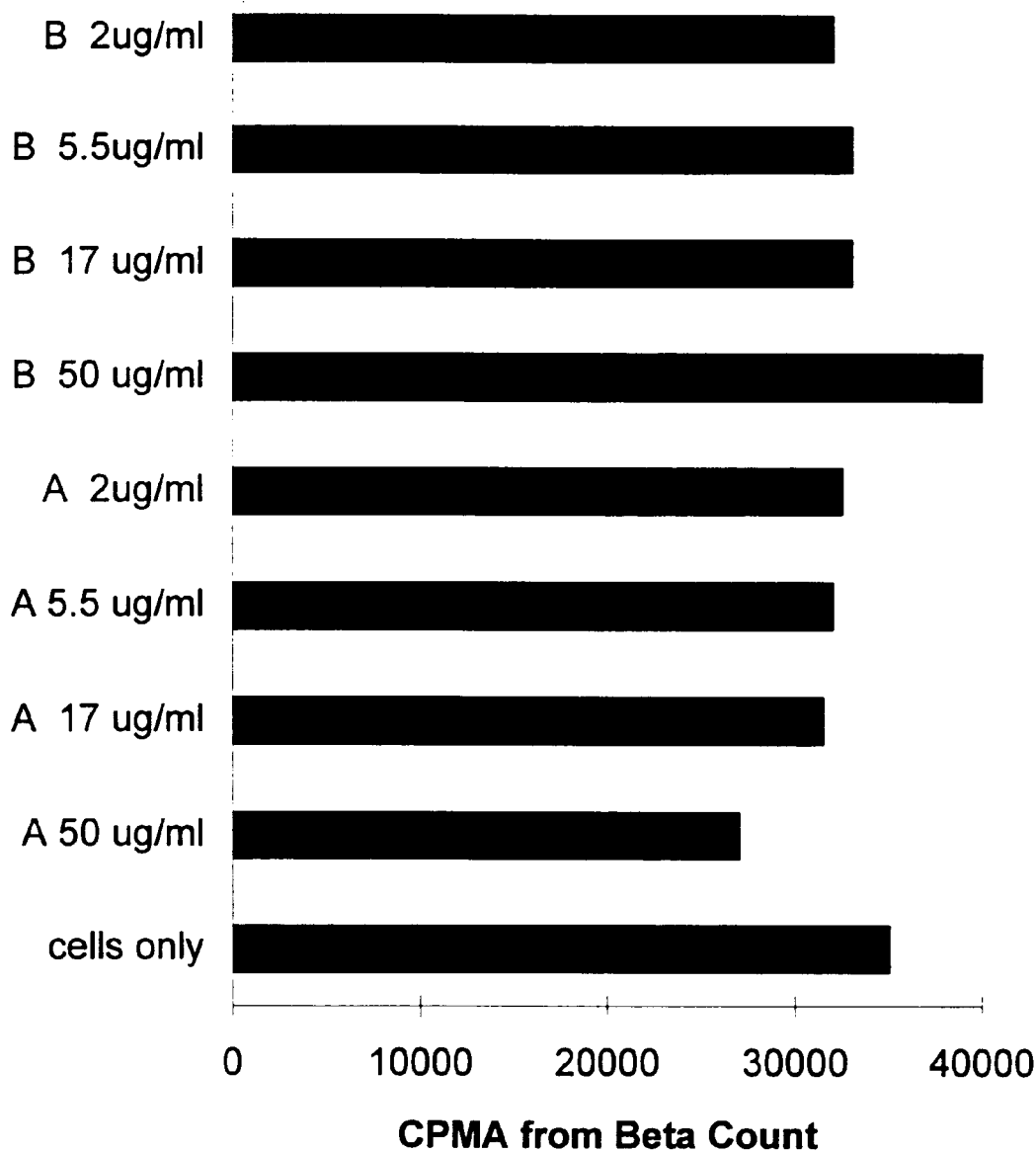

In further experiments, purified CON-1 protein was treated with PNGase, as set forth in Example 2 hereinabove, and tested in a alpha-glucosidase inhibition assay in comparison with the native glycosylated CON-1 protein. FIG. 8 shows that about 50 percent of the inhibitory activity is lost after deglycosylation. The remaining level of activity is still efficacious, but the result demonstrates that the carbohydrate moiety contributes some role in inhibition. One possibility is that, like some viral receptor systems in which glycosylation of the receptor protein strongly affects the binding avidity of the virus to its receptor, more of the unglycosylated protein is required to maintain the binding kinetics. Since definitive binding and other studies have not yet been performed, applicants do not intend to be bound by any particular theory of CON-1/CON-2's mechanism of action.

EXAMPLE 6

Effect of CON-1 Protein on the Infectivity of HIV

To test whether the alpha-glucosidase inhibitor activity of CON-1 could also intervene in HIV adsorption to target cells, thereby reducing infectivity and production of viral proteins, the following experiment was carried out: CEMx174 cells, as described by Hoxie, et al., J. Virol., 62: 2557 (1988), were infected at a concentration of 500,000 cells per ml for 2 hours at 37 degrees Centigrade with cell-free HIV-1, isolated as described in Alizon, et al., Nature, 312: 757 (1984), by adding virus at a concentration of 300 ng of HIV p24 protein per ml. Components of complete medium: RPMI 1640 with 10% fetal bovin serum, 2 mM L-glutamine, penicillin at 100 units/ml, and streptomycin at 100 ug/ml) with phytohemagglutin (PHA, 1 ug/ml; Sigma). After the 2 hour incubation, the virus inoculum was washed off and the cells were resuspended in complete culture medium containing various amounts of CON-1 protein. The cells were incubated in 96-well microtiter plates ($5\times10^4$ cells in 200 ul per well), and cell-free supernatants were collected 72 hours after infection.

The amount of HIV p24 in the cell-free supernatant was determined with a commercially available ELISA kit (Coulter) according to the manufacture's instructions. The HCEM cell line described in Pauza, et al. J. Virol., 63:3700 (1989) was used to assess the effect of CON-1 on HIV production from chronically infected cells. HCEM cells were pretreated with CON-1 at 10 ug/ml for 4 hours, washed twice with phosphate-buffered saline and then incubated at $10^6$ cells per ml in complete medium in the presence of CON-1 at 10 ug/ml, respectively. After 48 hours, cell-free supernatants were collected to determine HIV p24 levels by ELISA.

The results are shown in FIG. 9. Marked inhibition of p24 production is shown where cells were incubated at all concentrations above 1.25 ug/ml. Significant inhibition first occurs at 2.5 ug/ml of CON-1. In contrast, otherwise identical experiments performed in the presence of a control protein, Bovin serum Albumin, showed virtually no effect except a slight depression at the highest dose (20 ug/ml).

EXAMPLE 7

Experimental Details for Lys C. Digestion and Chromatography

1. Digestion of CON-1 protein.

500 ug of purified CON-1 protein was digested with 5 ug of Lys-c endoproteinase for 56 hr at 30°, in 0.1 ml of Tris-HCL buffer, pH 8.5 under sterile conditions. After digestion, the sample was loaded on a Sephadex G-50 column (110 cm×10 cm) previously equilibrated with double distilled water, and eluted with double distilled water. 2 ml/fractions were collected and analyzed for the inhibitory effect on alpha-glucosidase activity (FIG. 10). Those fractions showing potent inhibitory effect were pooled, vacuum dried and used for HPLC separation.

2. For HPLC separation, the dried sample was dissolved in HPLC grade water containing 0.1% trifluoracetic acid (TFA), and loaded on a C4 Vydac Column using a linear gradient from 10–110 min 0–100% B at 1.0 ml/min at 215 nm. Solvent A: 0.1%TFA in water/acetonitrile (95/5). Solvent B: 0.1% TFA in water/acetonitrile (25/75). 1 fraction per 2 min was collected manually. Finally, 200 ul of each fraction was vacuum dried and tested for inhibitory effect on alpha-glucosidase activity (FIG. 11).

(iii) The strategy for determining the structure of the glycopeptide is as follows:

The deduced amino acid sequence of the Con-1 protein and the effect of Lys-C cleavage predicted a lysine residue at the carboxyl end of the putative glycopeptide. Modification of the lysine residue by a specific reagent may modify the effect of the glycopeptide on alpha-glucosidase activity. Modification of the lysine residue by pyridoxal 5-phosphate reagent was carried out. Glycopeptide was preincubated with pyridoxal 5-phosphate, then tested for the inhibitory effect of pyridoxal 5-phosphate modified glycopeptide on alpha-glucosidase activity. It was found that the modified form of the glycopeptide surprisingly showed a 50% increase in inhibitory effect on alpha-glucosidase, and incidently confirming the reactivity of an epsilon amino group. Based on the deduced amino acid sequence of the Con-1 protein and the molecular weight of the putative glycopeptide as suggested by mass spectroscopy of fractions in the active peak after HPLC (FIG. 11), suggested that acetylglucosamine is likely N-linked to an asparagine residue. We therefore used N-acetylglucosaminidase to specifically cleave off acetylglucosamine from the glycopeptide, and then tested the inhibitory effect of the modified peptide on alpha-glucosidase activity. N-acetylglucosaminidase is known to specifically remove acetylglucosamine from asparagine amino acid by cleaving the N-linkage. It was found that the putative peptide lost about 20% of inhibition of alpha-glucosidase as compared to the nontreated glycopeptide, indicating that the glycopeptide contains an asparagine-linked acetylglucosamine residue. Finally, acetoaccetate reagent was used to test for the presence of glycine residue in the glycopeptide. The reagent was reacted with the putative glycopeptide, and the reaction product was tested for alpha-glucosidase activity. The acetoacetate glycopeptide complex not only caused the loss of inhibitory effect of the glycopeptide itself but is able to stimulate the alpha-glucosidase activity, indicating the native conformation of glycine residue of glycopeptide is important for inhibitory effect on alpha-glucosidase activity.

EXAMPLE 8

Cell Toxicity Studies In Vitro

T cell proliferation assay: CEM×179 cells (2×10 5/well in 200 ul of complete medium) were cultured during 6 days at 37° C. in flat-bottomed microtiter wells, and T cell proliferation was evaluated following a 6 hr pulse of (3H)-thymidine (0.5 uCi/well) (Amersham, Bucks, England). Cultures were harvested (Skatron Instruments, Lier, Norway) and the radioactivity was measured using a beta-counter (Packard Gamma 5500). The results indicated that up to 50 ug of Con-1 protein/assay showing no toxic effect on this cell line (FIG. 12).

EXAMPLE 9

Method of Making the Synthetic tetrapeptide Gylcyl-glycl-(NB-2-(acetylamino)-deoxy-2-B-pyranosyl)-asparaginyl-lysine The glycosylated tetra peptide was assembled by solid state peptide synthesis using an Applied Biosystems Inc. (Culver City Calif.) Model 432A Synergy peptide synthesizer. The peptide synthesis HMP resin-Fmoc-lysine(Boc-protected) and Fmoc glycine were purchased from Applied Biosystems. Na-Fmoc-N-B-(3,4,6-tri-O-acetyl-2-(acetylamino)-deoxy-2-B-glucopyranosyl)L-asparagine was purchased from Bachem (King of Prussia, Pa.). The synthesis was carried out at 25 umol scale. Standard coupling cycles were used except that a fixed 120 min coupling time was used to couple the glycolsylated asparagine residue. Following synthesis the peptide was cleaved and deprotected for 2 hours at room temperature in TFA containing 5% water. Peptide was precipitated by dripping the cleavage mixture through a disposable filtration column into cold t-butyl methyl ether. The precipitate was extracted twice with cold ether, then dried under vacuum. The peptide was dissolved in 1 ml of water and a small sample (0.5%) was retained for analysis. The crude material was freeze dried. Removal of the 3 acetyl groups from the glucopyranose ring was accomplished by dissolving the peptide in a 500 ml of methanol, then adding, while stirring, approximately 15 ml of sodium methoxide solution (30% methanol), sufficient to raise the pH of the reaction mixture to 12.5. The excess methoxide was quenched by adding approximately 10 ml glacial acetic acid to neutralize the reaction mixture. The reaction mixture was taken to dryness using a Speed-vac. The residue was dissolved in 200 ml of TFA and the peptide precipitated from this solution by dripping again into cold ether. After drying, the peptide was dissolved in water and freeze-dried.

EXAMPLE 10

Test of the Effect of Chemically Synthesized Glycopeptide on Alpha-Glucosidase Activity The freeze-dried glycopeptide whose structure was confirmed by mass spectroscopy (appended) was dissolved in 50 mM acetate buffer pH 5.6 and then used to examine the inhibitory effect on alpha-glucosidase activity. Following standard assay procedure for measuring the alpha-glucosidase activity, it was found that 10 ug of the synthetic glycopeptide gives about 90% inhibitory effect on the alpha-glucosidase activity compared to the control experiment.

What is claimed is:

1. A carrier glucosylated tetrapeptide comprising a tetrapeptide having the structure:

glycine-glycine-asparagine-lysine
|
acetylglucosamine, and a carrier.

2. A synthetic glycosylated pyridoxylated peptide having an enhanced alpha-glycosidase inhibitory activity compared to the inhibitory activity of the unmodified peptide comprising a tetrapeptide of primary structure:

glycine-glycine-asparagine-pyridoxyl-lycine
|
acetylglucosamine

3. An oral composition for alleviating excess uptake of simple sugars in treating diabetes comprising a bioactive fragment of CON-1 or CON-2 containing the structure:

glycine-glycine-asparagine-lycine
|
acetylglucosamine, in a pharmacologically effective dose encapsulated in an enteric coating.

4. An injectible composition for inhibiting proliferation of HIV-1 by inhibiting glycosylation in the HIV-1 growth cycle comprising a bioactive fragment of CON-1 or CON-2 having alpha-glucosidase inhibitory activity, dissolved in a physiologically compatible diluent.

5. A method of purifying CON-1 corresponding to SEQ ID NO:2 or CON-2 corresponding to SEQ ID NO:4, each having alpha-glucosidase inhibitory activity comprising heating a CON-1 or CON-2 containing mixture of proteins to a temperature and for a time sufficient to denature any proteases contained therein precipitating contaminants by the addition of alcohol recovering the supernatant sorbing protein recovered from said supernatant to hydroxyapatite and eluting CON-1 or CON-2 therefrom electrophoresing on a denaturing gel, and eluting CON-1 or CON-2 from the said gel.

* * * * *

UNITED STATES PATENT AND TRADEMARK OFFICE
CERTIFICATE OF CORRECTION

PATENT NO. : 5,981,720
DATED : November 9, 1999
INVENTOR(S) : Edwin A. Azen and David Pan It is certified that error appears in the above-identified patent and that said Letters Patent is hereby corrected as shown below:

In column 1, line 7, please add the following:

--STATEMENT REGARDING FEDERALLY SPONSORED RESEARCH OR DEVELOPMENT

This invention was made with United States government support awarded by the following agencies:

NIH    NIH Grant No. DEO3658

The United States government has certain rights in this invention.--

Signed and Sealed this

Seventeenth Day of October, 2000

*Attest:*

Q. TODD DICKINSON

*Attesting Officer*                    Director of Patents and Trademarks

UNITED STATES PATENT AND TRADEMARK OFFICE
CERTIFICATE OF CORRECTION

PATENT : 5,981,720
DATED : November 9, 1999
INVENTOR(S) : Edwin A. Azen and David Pan It is certified that error appears in the above-identified patent and that said Letters Patent is hereby corrected as shown below:

On the title page, please insert the following below item [76]:
--[73] Assignee: Wisconsin Alumni Research Foundation, Madison, Wisconsin--.

Signed and Sealed this

First Day of May, 2001

Attest:

NICHOLAS P. GODICI

*Attesting Officer*  *Acting Director of the United States Patent and Trademark Office*